United States Patent
Wilson

(10) Patent No.: US 7,153,329 B2
(45) Date of Patent: Dec. 26, 2006

(54) PROSTHETIC HIP JOINT WITH SIDE PIVOT

(76) Inventor: Michael T. Wilson, 2711 Cartwright Rd., Missouri City, TX (US) 77459-2602

(*) Notice: Subject to any disclaimer, the term of this patent is extended or adjusted under 35 U.S.C. 154(b) by 0 days.

(21) Appl. No.: 10/648,526

(22) Filed: Aug. 26, 2003

(65) Prior Publication Data

US 2005/0049719 A1    Mar. 3, 2005

(51) Int. Cl.
*A61F 2/60* (2006.01)
*A61F 2/78* (2006.01)

(52) U.S. Cl. .................................................. 623/33

(58) Field of Classification Search ............ 623/33–37, 623/27, 44, 45, 43
See application file for complete search history.

(56) References Cited

U.S. PATENT DOCUMENTS

| | | | | |
|---|---|---|---|---|
| 3,825,357 A | * | 7/1974 | Hilton ......................... 403/161 |
| 3,953,900 A | * | 5/1976 | Thompson .................... 623/39 |
| 4,215,441 A | | 8/1980 | Wilson ............................. 3/15 |
| 4,379,350 A | * | 4/1983 | Munny ......................... 623/39 |
| 4,488,320 A | | 12/1984 | Wilson ............................. 3/15 |
| 4,513,457 A | | 4/1985 | Glabiszewski .................... 3/15 |
| 4,634,446 A | * | 1/1987 | Kristinsson ..................... 623/33 |
| 4,846,842 A | * | 7/1989 | Connolly et al. .............. 623/43 |
| 4,904,270 A | | 2/1990 | Cooper ......................... 623/38 |
| 4,946,156 A | * | 8/1990 | Hart ............................. 482/66 |
| 5,267,950 A | * | 12/1993 | Weddendorf ................. 602/26 |
| 5,899,869 A | * | 5/1999 | Barrack et al. ............... 602/16 |
| 6,106,560 A | * | 8/2000 | Boender ....................... 623/44 |
| 6,322,594 B1 | * | 11/2001 | Boiten et al. ................. 623/27 |

* cited by examiner

*Primary Examiner*—Alvin J. Stewart
(74) *Attorney, Agent, or Firm*—Conley Rose, P.C.

(57) ABSTRACT

A prosthetic hip for supporting on a patient a prosthetic leg comprises a socket, a mount on the outer surface of the socket and defining a joint axis, the joint axis substantially coinciding with the natural axis of rotation of the patient's natural leg when rotated in a sagittal plane, and a first member adjustably affixed to the socket's outer surface. The first member includes an extension stop member and the upper end of the leg is pivotably mounted on the mount such that and pivoting of the leg in at least one direction is limited by the stop member. The prosthetic hip may also include a roller on a load arm extending medially from the upper leg end so as to engage the outer surface of the socket transmit a load from the socket directly to the prosthetic leg.

13 Claims, 8 Drawing Sheets

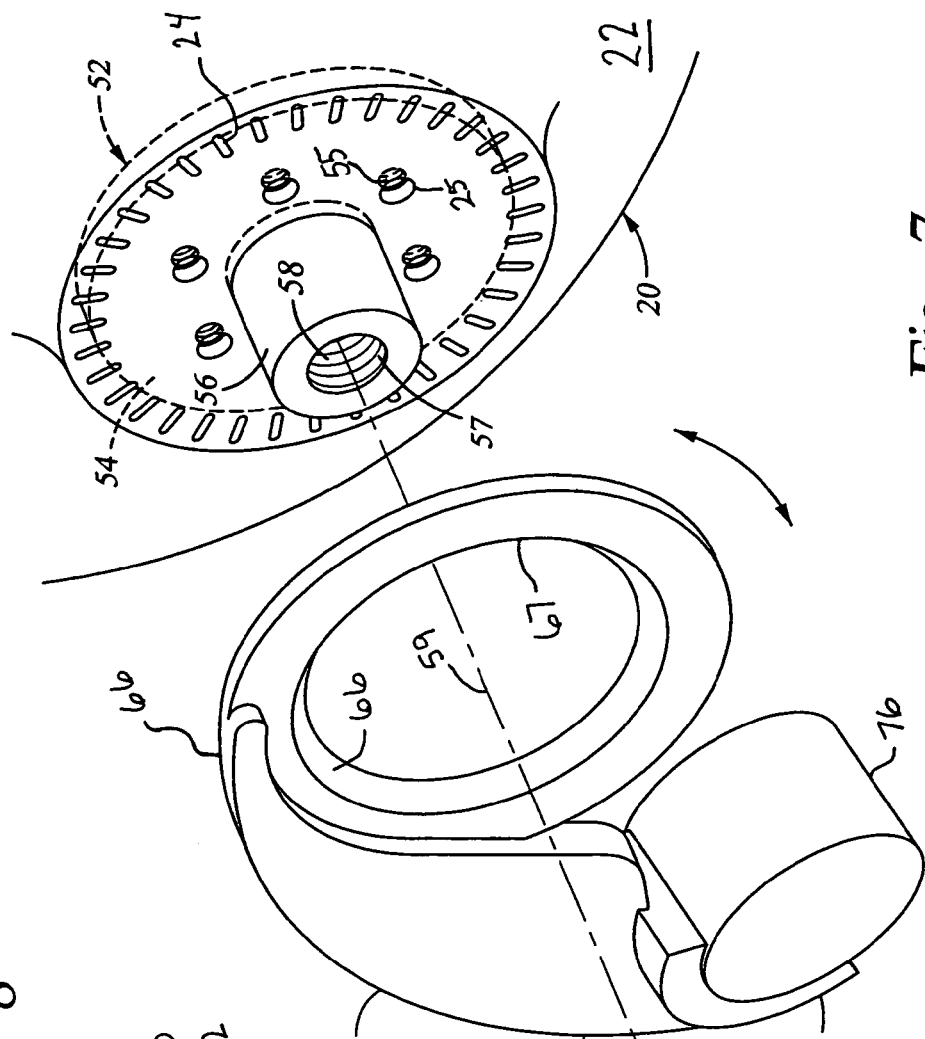
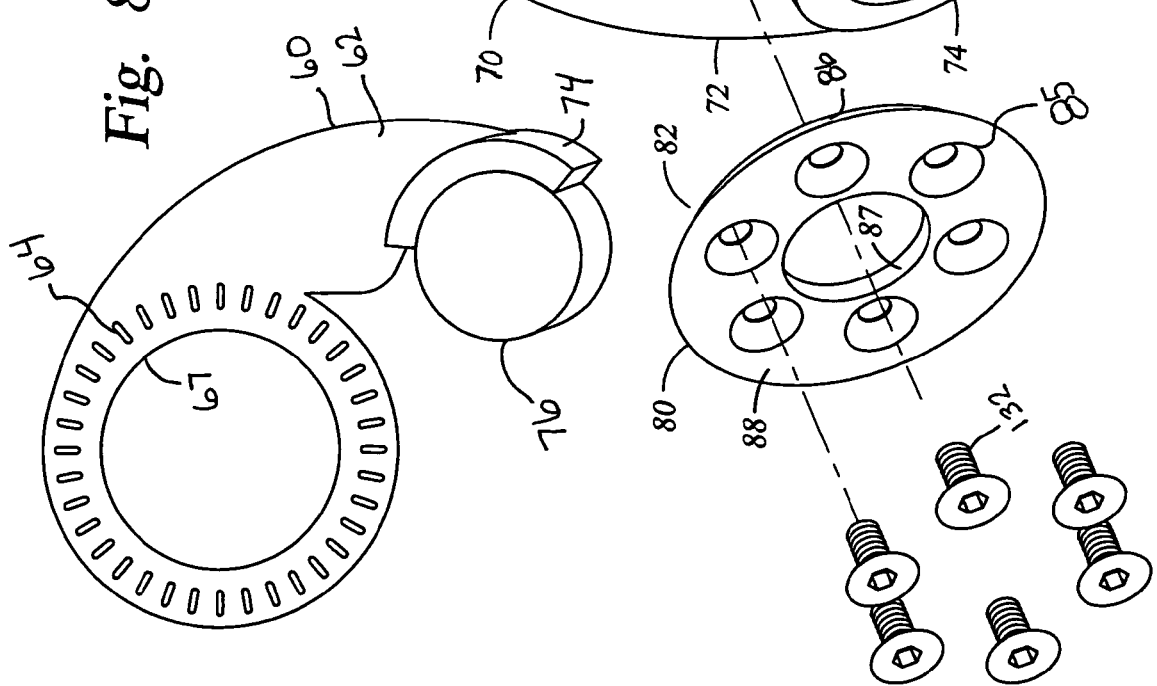

PROSTHETIC HIP JOINT WITH SIDE PIVOT

TECHNICAL FIELD OF THE INVENTION

The present invention relates generally to a prosthetic hip designed to provide a pivoting motion that closely resembles that of a natural hip joint. More particularly, the present invention relates to a prosthetic hip having a side pivot point and an aligned load point.

BACKGROUND OF THE INVENTION

When it is necessary to amputate a diseased or damaged leg from a human being, the amputation is typically performed in one of two ways. Hip disarticulation amputations are surgical procedures in which the leg is removed at the hip joint, leaving the pelvis substantially intact. Hemipelvectomy amputations are surgical procedures in which a portion of the pelvis is removed along with the leg. Amputees who have undergone either procedure often wish to be fitted with prosthetic equipment that will allow them to replicate at least a portion of the function of the missing limb. Typically, this entails creation of both a prosthetic hip joint and artificial leg. Artificial legs are well known in the art and are widely available with a variety of features.

Likewise, prosthetic hips are well known in the art, and several such hips have been designed. A typical conventional prosthetic hip includes a socket that receives and is affixed to the lower portion of the torso of the amputee and a pivotable joint that connects the socket to the artificial leg. The joint is intended to allow the artificial leg to pivot relative to the socket so as to simulate the relative movement that is provided by a natural hip joint. Conventional prosthetic hips, however, use a configuration in which the joint is positioned on the front of the socket, as shown in FIG. 1. This configuration is premised on the assumption that, by positioning the hip joint in this manner, it will be easier for the amputee to stand and walk as desired and to maneuver the artificial leg in general.

This conventional configuration has certain disadvantages. For example, because the hip joint itself is not aligned with the natural weight-bearing line of the amputee's body, an unnatural load is applied to the torso of the amputee and a sizable moment occurs at the joint itself. In addition, the forward position of the joint makes it difficult to construct a cosmesis that can effectively maintain the desired cosmetic effect when the amputee is in a sitting position.

Hence, it remains desirable to provide a improved prosthetic hip for use with an artificial leg. The desired prosthetic hip would avoid the disadvantages of the prior art and would provide stable and comfortable support to the amputee.

SUMMARY OF THE INVENTION

The present invention comprises a prosthetic hip having a side pivot point and a vertically aligned load point that is offset from the pivot point. The present prosthetic hip avoids the disadvantages of the prior art by positioning the load-bearing member directly below, rather than in front of, the load point of the amputee's torso within the socket.

In certain embodiments, the invention relates to a prosthetic hip for supporting a prosthetic leg, comprising a socket having an outer surface, a mount on the outer surface and defining a joint axis, the joint axis substantially coinciding with the natural axis of rotation of the patient's natural leg when rotated in a sagittal plane; and a first member adjustably affixed to the outer surface, the first member including an extension stop member; the upper leg end being pivotably mounted on the mount such that the leg is pivotable about the joint axis and pivoting of the leg in at least one direction is limited by the extension stop member.

BRIEF DESCRIPTION OF THE DRAWINGS

For a detailed description of a preferred embodiment of the invention, reference will now be made to the accompanying drawings wherein:

FIG. 7 is a further exploded view of the hip joint of FIG. 4;

FIG. 8 is an enlarged view of one component of a preferred embodiment of the present invention.

DETAILED DESCRIPTION OF THE INVENTION

Figure 1:
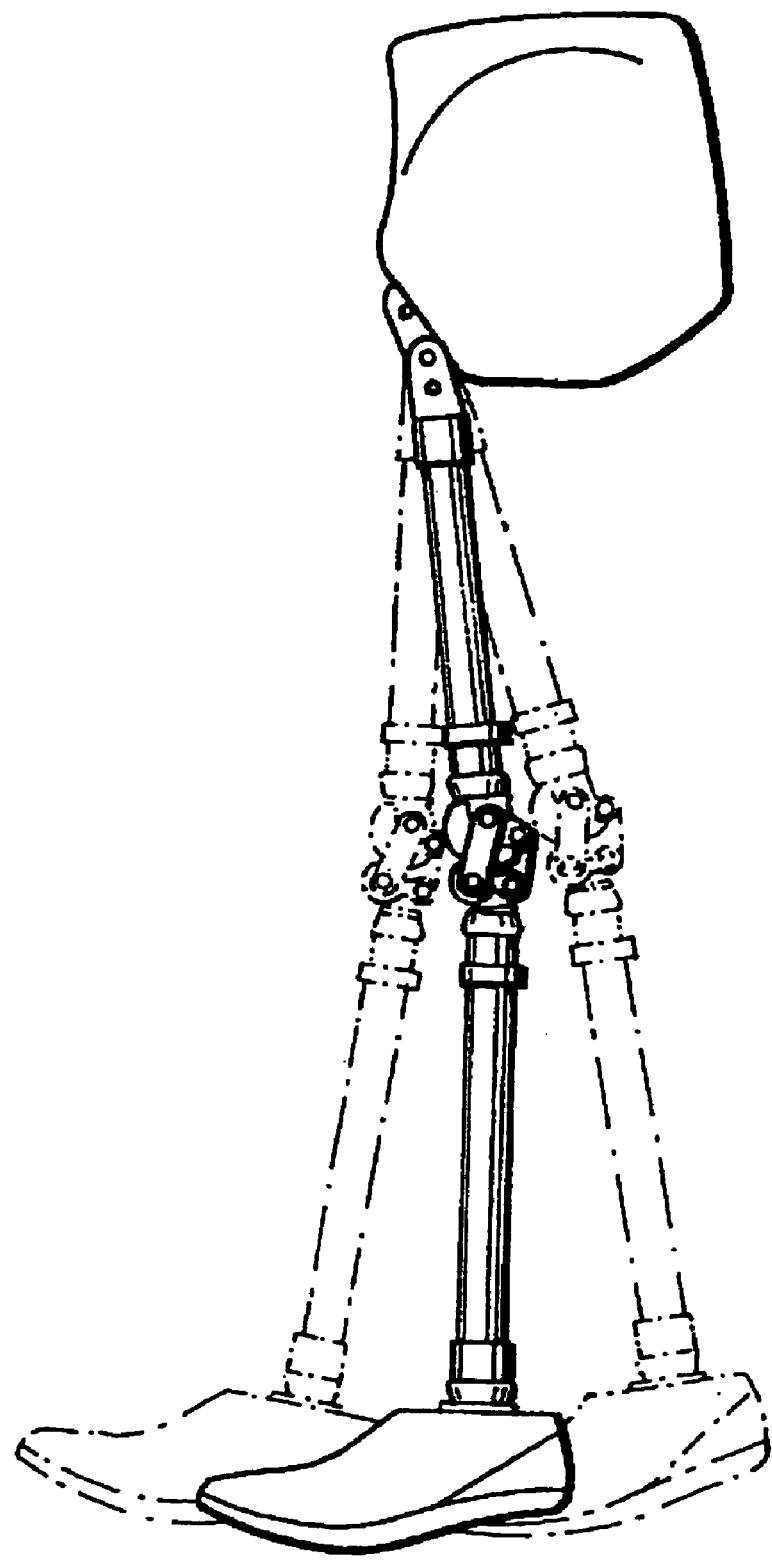
FIG. 1 is a side schematic view of a conventional prosthetic hip and leg.
Figure 2:
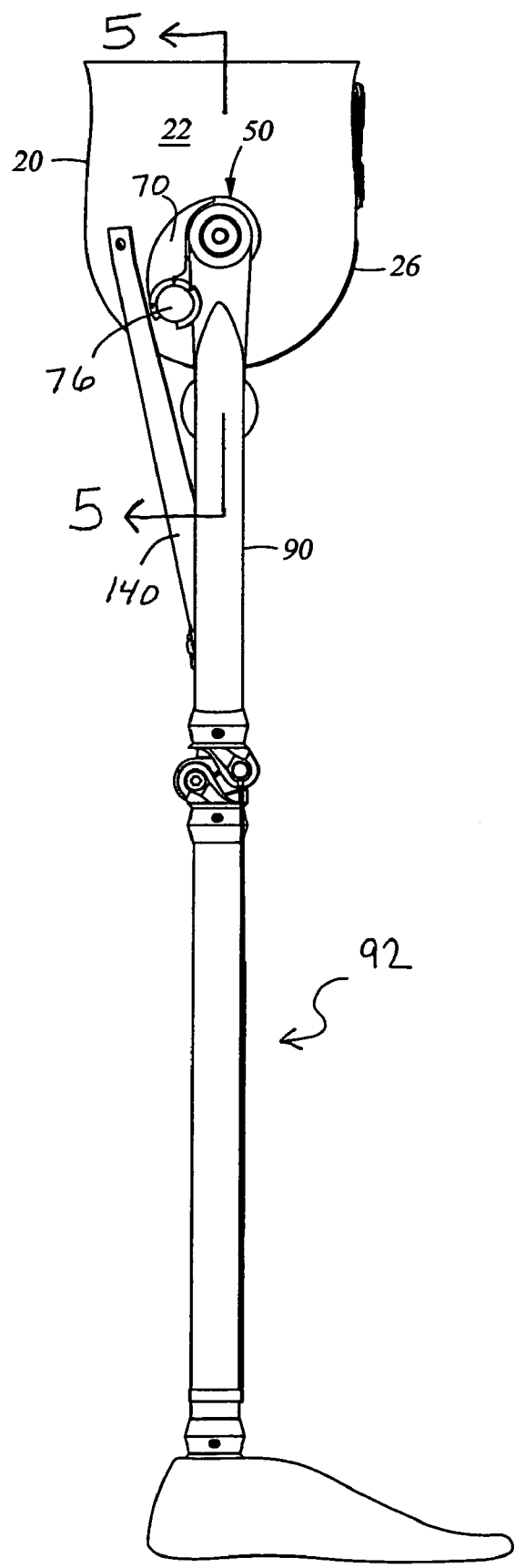
FIG. 2 is a side elevation of a prosthetic hip constructed in accordance with a preferred embodiment of the present invention and used in conjunction with a prosthetic leg.
Figure 3:
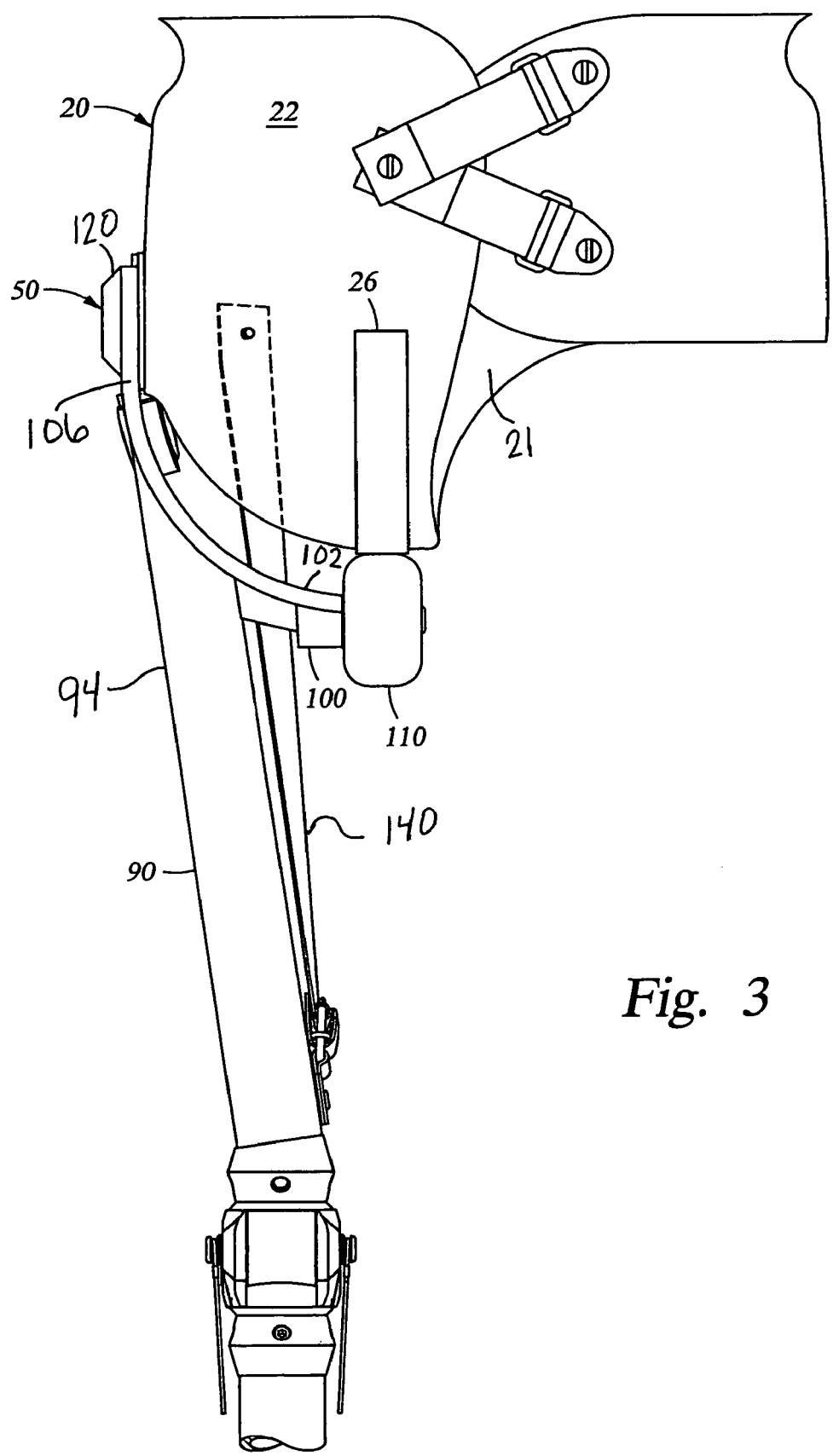
FIG. 3 is a front view of the prosthetic hip of FIG. 2.

Referring now to FIGS. 2 and 3, the prosthetic hip 10 of the present invention includes a socket 20, a hip joint 50, and a load arm 100. Hip joint 50 is affixed to the side of socket 20 as described in detail below. Hip joint 50 serves to pivotally connect a femur 90 of an artificial leg 92 to socket 20. As further described below, in some embodiments, load arm 100 extends laterally from a point near the upper end of femur 90 to a point in a vertical plane that approximately intersects the natural hip joint.

Socket

As is known in the art, socket 20 is preferably constructed of fiber-reinforced plastic (FRP) and is preferably formed around a mold of the amputee's torso so that it provides a snug, customized fit. In this regard, any suitable technique for constructing and shaping socket 20 may be used. Socket 20 has an inner surface 21 and an outer surface 22. In a departure from conventional sockets, however, socket 20 includes a mount for hip joint 50 that is positioned on the side, rather than on the front, of socket 20. Put another way, as best illustrated in FIG. 2, hip joint 50 is positioned so that it lies in or near a coronal plane intersecting both of the amputee's natural hip joints, hereinafter referred to as the hip joint plane. The coronal plane is perpendicular to the plane of the paper in FIG. 2 and parallel to the plane of the paper in FIG. 3. The present mounting of hip joint 50 is in contrast to conventional sockets, which have the hip joint mounted well in front of the hip joint plane. At the same time, hip joint 50 is mounted on socket 20 such that the plane of rotation of hip joint 50 is substantially parallel to the natural plane of rotation of the amputee's missing leg.

According to some embodiments, the outer surface 22 of socket 20 includes a roller track 26. Roller track 26 is preferably substantially smooth and describes a portion of a circular path lying in a sagittal plane and having its center point at or near the center of rotation of the amputee's natural hip joint. Roller track 26 is discussed in further detail below.

Hip Joint

Figure 4:
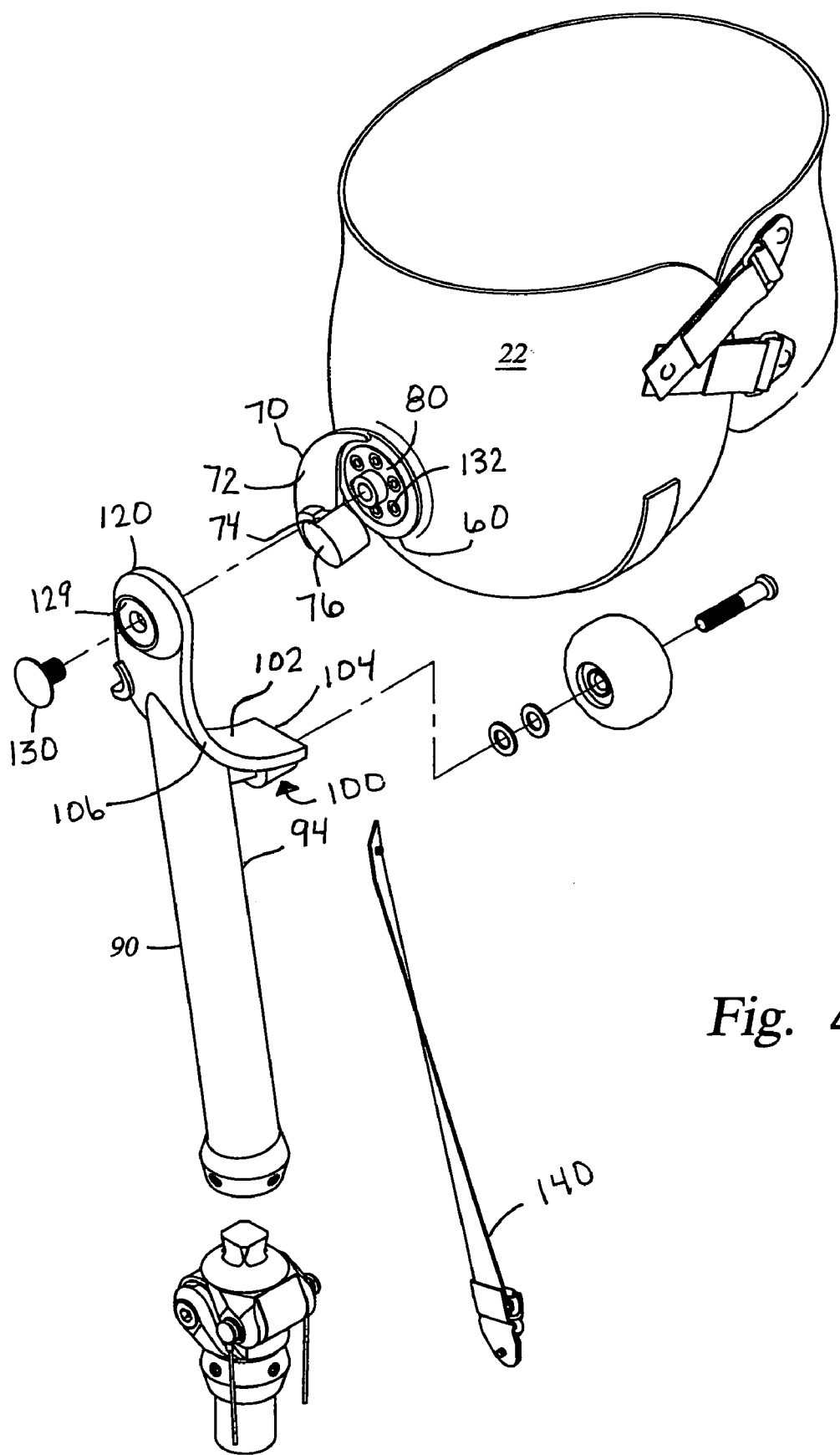
FIG. 4 is an exploded view of the prosthetic hip of FIG. 2.
Figure 5:
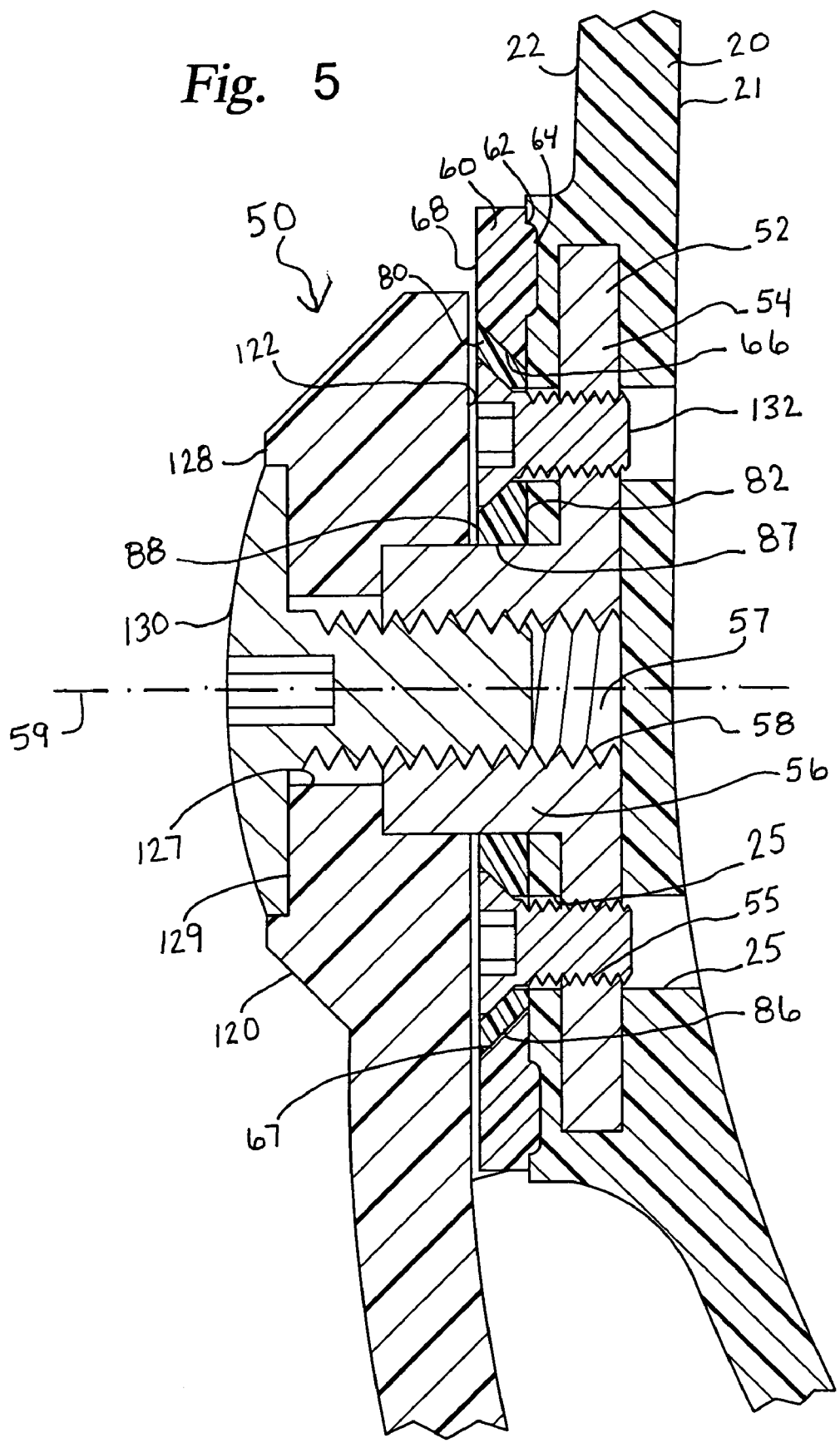
FIG. 5 is an enlarged cross-section take along the lines 5–5 of FIG. 2.
Figure 6:
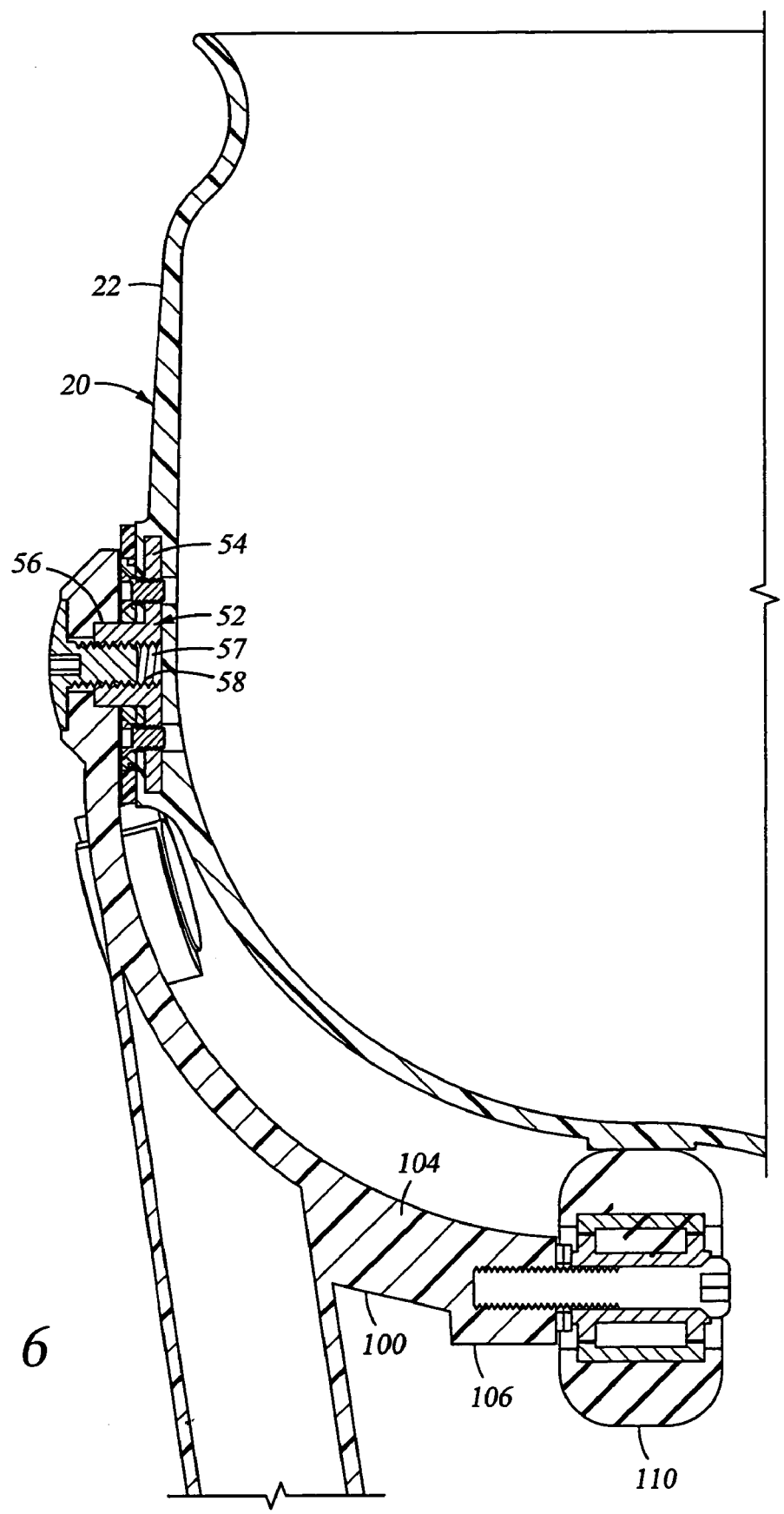
FIG. 6 is a cross-section of a hip joint constructed in accordance with an alternative embodiment of the present invention.

Hip joint 50 is preferably constructed so as to allow substantially free rotation of the artificial leg within certain prescribed limits. Limits on rotation of the leg are described in detail below. Referring now to FIGS. 4–6, some embodiments of hip joint 50 include a mount 52, which is preferably embedded in and integral with socket 20, a locking plate 60, and a tightening plate 80. Mount 52 preferably includes a head 54 and an extension 56 having a bore 57 that includes female threads 58 and defines a joint axis 59. Head 54 is preferably embedded in the material of socket 20 at the time socket 20 is formed. Extension 56 extends outwardly from the outer surface of socket 20. Head 54 and extension 56 are preferably but not necessarily formed as a single metal piece.

Locking plate 60 preferably has an inner surface 62, an outer surface 68, and a bore 67 therethrough. As best shown in FIGS. 7 and 8, inner surface 62 preferably includes a plurality of ridges 64, which are preferably but not necessarily configured such that they are parallel to radii extending from the center of bore 67. In a preferred embodiment, outer surface 22 of socket 20 includes a similar plurality of similarly configured ridges 24. Outer surface 68 of locking plate 60 preferably includes a frustoconical bevel 66 (FIG. 7) centered on bore 67.

Referring briefly again to the embodiments shown in FIGS. 2, 6, and 7, locking plate 60 further includes an extension stop 70 that extends substantially radially away from bore 67. Extension stop 70 comprises an arm 72 and an arcuate stop member 74 supported on the distal end of arm 72. Stop member 74 preferably extends outwardly from the outer surface of locking plate 60 and is preferably substantially perpendicular to the arm 72. Stop member 74 preferably receives and supports a generally cylindrical elastomeric bumper 76 mounted therein.

Referring now to FIGS. 2, 5, and 7, tightening plate 80 preferably has an inner surface 82, and outer surface 88, and a central bore 87. Tightening plate 80 preferably has a frustoconical side edge 86, whose shape corresponds to that of bevel 66. In addition, tightening plate 80 includes at least one, and preferably at least 5 or 6 countersunk holes 85, which correspond in position to a similar plurality of threaded or unthreaded holes 25 in socket 20 and threaded holes 55 in head 50.

Figure 9:
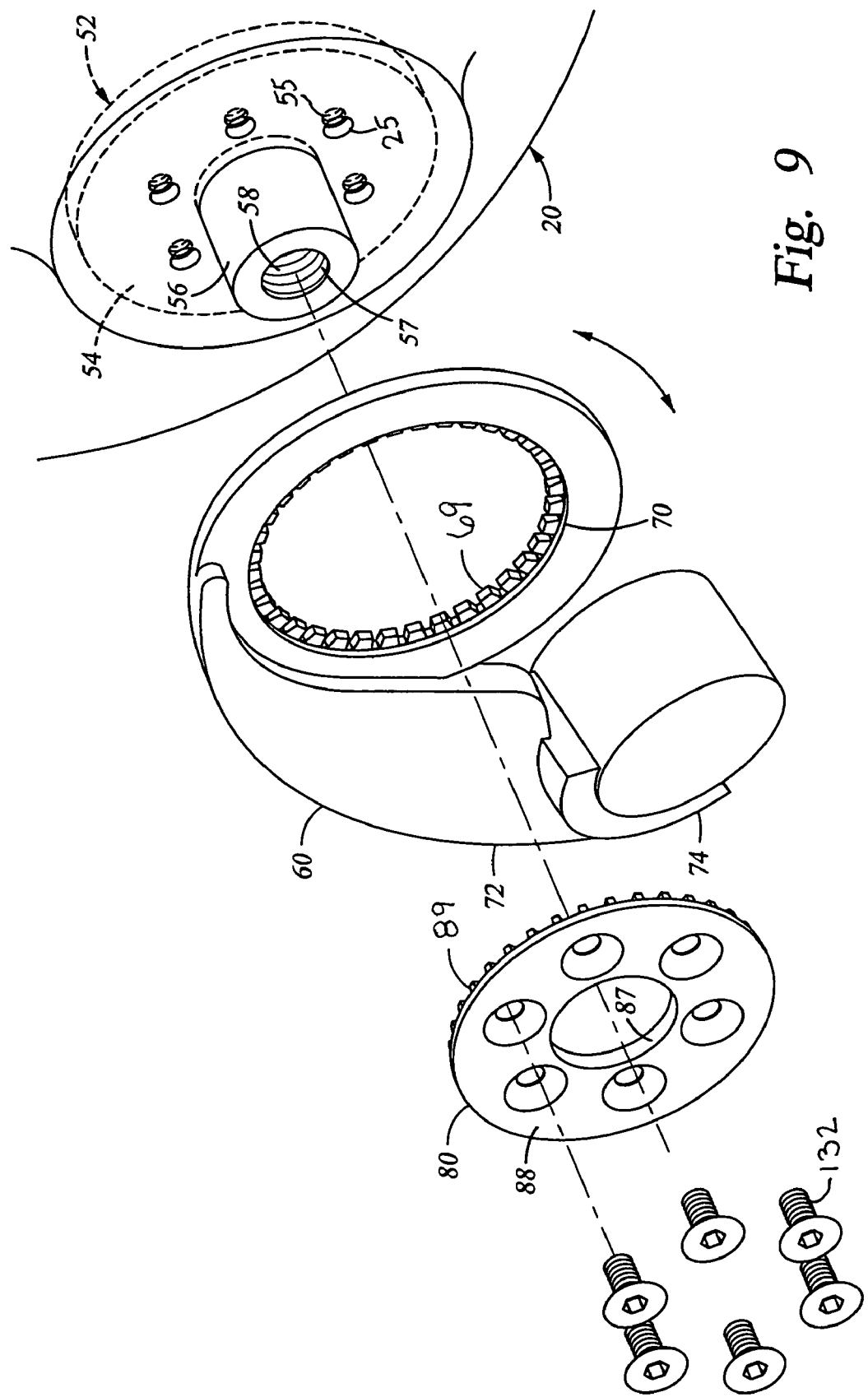
FIG. 9 is an exploded view of an alternative embodiment of the components of FIG. 7.

In an alternative embodiment, illustrated in FIG. 9, locking plate 60 is provided with a plurality of teeth or ridges 69 that engage a plurality of corresponding teeth or ridges 89 on tightening plate 80. The engagement of teeth 69 with teeth 89 serves to prevent rotation of locking plate 60 relative to socket 20, as tightening plate 80 is affixed to socket 20 (such as by the engagement of screws 132 in threaded holes 55).

It will be understood that the systems for positioning and preventing rotation of locking plate 60 that are shown in FIGS. 7 and 9 are merely preferred embodiments. Any alternative means for achieving these objectives can be substituted therefore and is intended to be within the scope of the present invention.

Load Arm

Referring now to FIGS. 3 and 6, in some embodiments load arm 100 comprises a body 102 having an inner end 104 and an outer end 106. Inner end 104 is adapted to support thereon a pivotally mounted roller 110. Roller 110 is mounted such that its axis of rotation is substantially horizontal and parallel to the hip joint plane. The outer end 106 of load arm 100 can be affixed to the artificial leg in a variety of ways. At least two configurations are possible. In the configuration shown in the Figures, load arm 100 is constructed as an integral part of the upper end of the artificial femur 90. In the second (not shown), load arm 100 is separate from femur 90 and is mechanically affixed to femur 90 by any suitable means. There are advantages associated with each configuration. For example, an integral load arm has few components and fewer interfaces, but is not adjustable and may be more complicated to manufacture.

Referring still to FIGS. 3 and 5, the artificial femur 90 used with the present hip joint is preferably a rod having a conventional artificial knee attached to its lower end. The upper end of the rod is integral with or rigidly affixed to a connector 120 that is adapted to pivotally engage hip joint 50. In some embodiments, connector 120 includes at least a flattened head 121 having an inner surface 122, an outer surface 128, and bore 127 therethrough. In a preferred embodiment, inner surface 122 includes a countersink 123 surrounding bore 127 and outer surface 128 includes a countersink 129 surrounding bore 127. Countersinks 123 is configured to receive extension 56 of mount 50 and countersink 129 is configured to receive the head of a screw 130, as described below. If desired, one or both of countersinks 123, 129 may each be further configured to additionally receive a washer (not shown).

Assembly

When it is desired to assemble the present prosthetic hip 10, locking plate 60 and tightening plate 80 are aligned and placed on mount 52 so that extension 56 extends through their respective bores 67, 87. At this point, it is possible and desirable to position locking plate 60 such that its extension stop member 74 is at a desired azimuthal position relative to joint axis 59. Once locking plate 60 is rotated to the desired position, locking plate 60 is pressed against the outer surface 22 of socket 20 such that ridges 64 engage ridges 24 and prevent locking plate 60 from rotating relative to socket 20. Tightening plate 80 is likewise pressed against locking plate 60 such that its frustoconical edge 86 bears on bevel 66. Screws or other fasteners 132 may then be inserted through holes 85 and tightened into corresponding holes 55 so that locking plate 60 is held in place and cannot rotate relative to socket 20.

Connector 120 at the upper end of the artificial femur is then placed over mount 52 such that its bore 127 aligns with bores 67, 87 of locking plate 60 and tightening plate 80, respectively. If desired, a washer may be included between the inner surface 122 of connector 120 and the outer surface 88 of tightening plate 80. A screw 130 is then passed through bore 127 and threaded into the threaded bore 57 of mount extension 56. If desired, a washer may also be included between the outer surface 128 of connector 120 and the head of locking screw 130. According to one preferred embodiment, locking screw 130 may be an expandable screw such as are known in the art. In this embodiment, screw 130 is locked in place by driving a compression member (not shown) through an opening (not shown) in the inner surface 21 of socket 20, into a bore (not shown) in locking screw 130 so as to radially expand screw 130 and prevent it from loosening during use.

Lastly, it is preferred to provide an energy storing means 140 between socket 20 and the prosthetic leg 90. This can be an elastic band 140, as shown in the Figures, or can be any other suitable energy storing means. It is preferred that energy storing means 140 be affixed to the outside of socket 20 in a manner that allows it to substantially avoid interference with joint 50 when the prosthetic hip is flexed.

Once the joint has been completely assembled, it is possible to rotate prosthetic femur 90 in a sagittal plane. Because hip joint 50 lies substantially in the hip joint plane, the rotation will simulate the rotation of a natural leg in a sagittal plane. This is in contrast to conventional hip prostheses, which place the axis of rotation for the leg in front of the hip joint plane.

Load arm 100 is preferably configured such that when the user places his weight on the prosthesis, the joint assembly deforms sufficiently to allow outer surface 22 of socket 20 to bear on roller 110 so that the load is transferred from socket 20 to leg 90 via roller 110 and arm 100, rather than via hip joint 50. As the patient moves his body forward with his weight on the prosthesis, the prosthetic leg is extended backward until it contacts stop member 74. Thus, stop member 74 and extension stop 70 serve to prevent the prosthetic leg from extending too far backward. During this process, roller 110 bears on track 26. As the patient shifts his weight to his natural leg and removes his weight from the prosthesis, socket 20 lifts slightly off roller 26 and the prosthetic leg can be swung forward until it is stopped by the resistance of energy storing means 140. As the leg reaches the end of its forward swing, the patient allows the heel of the prosthesis to contact the ground. The patient can then either move his body forward in a continuing stride, again placing his weight on the prosthesis, or can cease walking and place all or a portion of his weight on the prosthesis while standing still.

It is preferred that extension stop 70 be positioned during assembly or fitting of the prosthesis such that the rearward extension of the prosthesis is optimized for the patient. As described above, once the desired degree of extension has been determined, locking plate 60 is tightened against the outer surface of socket 20 so that further rotation is precluded.

Because roller track 26 provides an interface for the transfer of a mechanical load from socket 20 to femur 90, the present prosthetic hip joint allows the wearer to load her prosthetic leg in a more natural manner. For example, the patient can bend forward at the hip or be seated without the unnatural hip/leg relationships that result in a hip prosthesis that has the hip joint in front of the socket. Furthermore, load arm 100 allows the mechanical load to be transferred to the prosthetic leg without the load being transmitted through the joint itself. This in turn allows the joint 50 to be more compact.

It is believed that one of ordinary skill in the art of prosthetics manufacturing will be able to select suitable materials from which to construct the components of the present invention. Nonetheless, certain materials are suggested herein because they are exemplary of suitable materials. The disclosure of various materials herein is not intended to limit the scope of the claims in any way. Socket 20 is preferably constructed of fiber reinforced plastic. Similarly, locking plate 60, with its integral extension stop member 70 are preferably formed of titanium. Tightening plate 80 may be constructed of titanium or stainless steel. Connector 120 preferably comprises aluminum, titanium, or fiber-reinforced plastic, while the femur to which it is attached comprises titanium or another suitable light but strong metal alloy or polymer.

Several useful discussions of the context and usage of prosthetic feet and legs are given in U.S. Pat. Nos. 5,625,596, 5,482,513, 5,443,527, 5116,384, which are all incorporated herein in their entireties. For example, the construction of a suitable cosmesis, prosthetic leg attachment, and composition of various components can be derived from those disclosures.

While a preferred embodiment of the invention has been shown and described, modifications thereof can be made by one skilled in the art without departing from the spirit of the invention. For example, the precise shape of the components, the materials of which they are constructed, the degree of movement that is allowed in each direction, and other aspects of the invention can be changed without departing from the spirit of the invention. The ridges used to prevent relative rotation between the extension stop and the socket are preferred but can be replaced with any other suitable device, including but not limited to teeth, high-friction inserts, locking washers, or the like, or can be eliminated entirely. In other embodiments, the extension stop may be fused or adhered to socket 20, although this eliminated the desired adjustability of the extension stop. Similarly, the shape of the extension stop may be modified, so long as it is capable of engaging and stopping extension of the prosthetic leg.

What is claimed is:

1. A prosthetic hip, comprising:
    a socket having an outer surface;
    a mount on said outer surface, said mount defining a joint axis, said mount being positioned on said surface such that said joint axis substantially coincides with the natural axis of rotation of the patient's natural leg when rotated in a sagittal plane; and
    a first member adjustably affixed to said outer surface, said first member including a stop member;
    a prosthetic leg having an upper leg end wherein the upper leg end is pivotably mounted on said mount and includes a load arm extending medially from the upper leg end so as to engage the outer surface of the socket such that the prosthetic leg is pivotable about said joint axis and pivoting of the leg in at least one direction is limited by said stop member;
    wherein said load arm is configured so as to transmit a load from the socket directly to the prosthetic leg and includes a roller at its distal end and wherein said roller engages the outer surface of said socket.

2. The prosthetic hip according to claim 1 wherein the outer surface of said socket includes a roller track configured to engage said roller.

3. The prosthetic hip according to claim 1 wherein said first member is mounted on said mount between said socket and said upper leg end.

4. The prosthetic hip according to claim 1 wherein said first member is azimuthally positionable relative to said joint axis, further including means for preventing rotation of said first member relative to said socket.

5. The prosthetic hip according to claim 4 wherein said rotation preventing means comprises at least a first engaging means on said first member and at least a second engaging means, said second engaging means being fixed relative to said joint axis, said first and second engaging means being engageable to prevent rotation of said first member relative to said socket.

6. The prosthetic hip according to claim 5 wherein said second engaging means comprises at least one protrusion on said socket.

7. A prosthetic hip system, comprising:
a socket having an outer surface;
a mount on said outer surface, said mount defining a joint axis, said mount being positioned on said surface such that said joint axis passes through the patient's natural hip joint;
a prosthetic leg having an upper leg end, said upper leg end being pivotably mounted on said mount such that the prosthetic leg is pivotable about said joint axis during walking, said upper leg end including a load arm extending medially therefrom end so as to engage the outer surface of the socket, wherein said load arm is configured so as to transmit a load from the socket directly to the prosthetic leg and wherein said load arm includes a roller at its distal end and said roller engages the outer surface of said socket; and
means for limiting pivoting of the leg about said joint axis in at least one direction.

8. The prosthetic hip according to claim 7 wherein the outer surface of said socket includes a roller track configured to engage said roller.

9. The prosthetic hip according to claim 7 wherein said stop member includes means for engaging said socket so as to prevent relative rotation between said socket and said stop member.

10. The prosthetic hip according to claim 7 wherein said first member is mounted on said mount between said socket and said upper leg end.

11. The prosthetic hip according to claim 7 wherein said first member is azimuthally positionable relative to said joint axis, further including means for preventing rotation of said first member relative to said socket.

12. The prosthetic hip according to claim 11 wherein said rotation preventing means comprises at least a first engaging means on said first member and at least a second engaging means, said second engaging means being fixed relative to said joint axis, said first and second engaging means being engageable to prevent rotation of said first member relative to said socket.

13. The prosthetic hip according to claim 12 wherein said second engaging means comprises at least one protrusion on said socket.

* * * * *